US00PP34418P2

(12) United States Plant Patent
Wood

(10) Patent No.: US PP34,418 P2
(45) Date of Patent: Jul. 12, 2022

(54) ***HYDRANGEA* PLANT NAMED 'SMNHRL'**

(50) Latin Name: ***Hydrangea* x *arborescens* subsp. *radiata***
Varietal Denomination: 'SMNHRL'

(71) Applicant: Spring Meadow Nursery, Inc., Grand Haven, MI (US)

(72) Inventor: Timothy D Wood, Spring Lake, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/483,228

(22) Filed: Sep. 23, 2021

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Karen M Redden
(74) *Attorney, Agent, or Firm* — Cassandra Bright

(57) ABSTRACT

A new and distinct cultivar of *Hydrangea* plant named 'SMNHRL' is disclosed, characterized by large, mophead inflorescences with red-pink flowers, and dark green foliage. Sepals open a vivid green, turning whitish-green. Plants are vigorous with upright habits. The new variety is a *Hydrangea*, typically produced as an outdoor ornamental plant.

3 Drawing Sheets

Latin name of the genus and species: *Hydrangea* x *arborescens* subsp. *radiata.*

Variety denomination: 'SMNHRL'.

BACKGROUND OF THE INVENTION

The new cultivar is a product of a planned breeding program conducted by the inventor, at a commercial nursery in Grand Haven, Mich. The objective of the breeding programs was to produce new *Hydrangea* varieties with large flower heads, and strong, upright stems. The open-pollination resulting in the new variety was made during 2011.

The parent varieties cannot be identified as this new selection resulted from an open-pollination in which seed bulk was collected from various seed parents.

The new variety was found and selected by the inventor in 2015 at the same nursery in Grand Haven, Mich.

Asexual reproduction of the new cultivar 'SMNHRL' was first performed during 2015 in Grand Haven, Mich., by softwood cuttings. Through subsequent propagation, multiple additional generations have been reproduced, having shown that the unique features of this cultivar are stable and reproduced true to type.

SUMMARY OF THE INVENTION

The cultivar 'SMNHRL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHRL'. These characteristics in combination distinguish 'SMNHRL' as a new and distinct *Hydrangea* cultivar:

1. Very large mophead inflorescences.
2. Strong, upright stems.

3. Sepals open a vivid green, turning whitish-green.
4. Red-pink petals on infertile flowers create a colorful "eye".
5. Dark green foliage.

PARENT COMPARISONS

The parent varieties cannot be accurately identified for comparison.

COMMERCIAL COMPARISON

Plants of the new cultivar *Hydrangea* 'SMNHRL' can be compared to the commercial variety *Hydrangea* 'Annabelle', unpatented. Plants of 'SMNHRL' are similar to plants of 'Annabelle' in most horticultural characteristics, however, plants of 'SMNHRL' differ in the following:

1. 'SMNHRL' has a hemispherical shaped inflorescence, while 'Annabelle' has a rounded shaped inflorescence.
2. Inflorescence color of 'SMNHRL' varies from vibrant green to whitish-green, while inflorescence color of 'Annabelle' is white.
3. 'SMNHRL' has red-pink petals with a bright colored "eye", while 'Annabelle' has white central petals and sepals.

Plants of the new cultivar *Hydrangea* 'SMNHRL' can be compared to the commercial variety *Hydrangea* 'SMNHALR', U.S. Plant Pat. No. 28,858. Plants of 'SMNHRL' are similar to plants of 'SMNHALR' in most horticultural characteristics, however, plants of however, plants of 'SMNHRL' differ in the following:

1. 'SMNHRL' has darker green foliage than 'SMNHALR'.
2. 'SMNHRL' has red-pink petals in the center of infertile flowers. 'SMNHALR' has lighter pink central petals.
3. Sepals of 'SMNHRL' turn whitish-green with maturity, while sepals of 'SMNHARL' turn entirely white.

BRIEF DESCRIPTION OF THE PHOTOGRAPHS

'SMNHRL' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Hydrangea*. Age of the plants photographed is between 2 to 3 years.

DETAILED BOTANICAL DESCRIPTION

Figure 1:
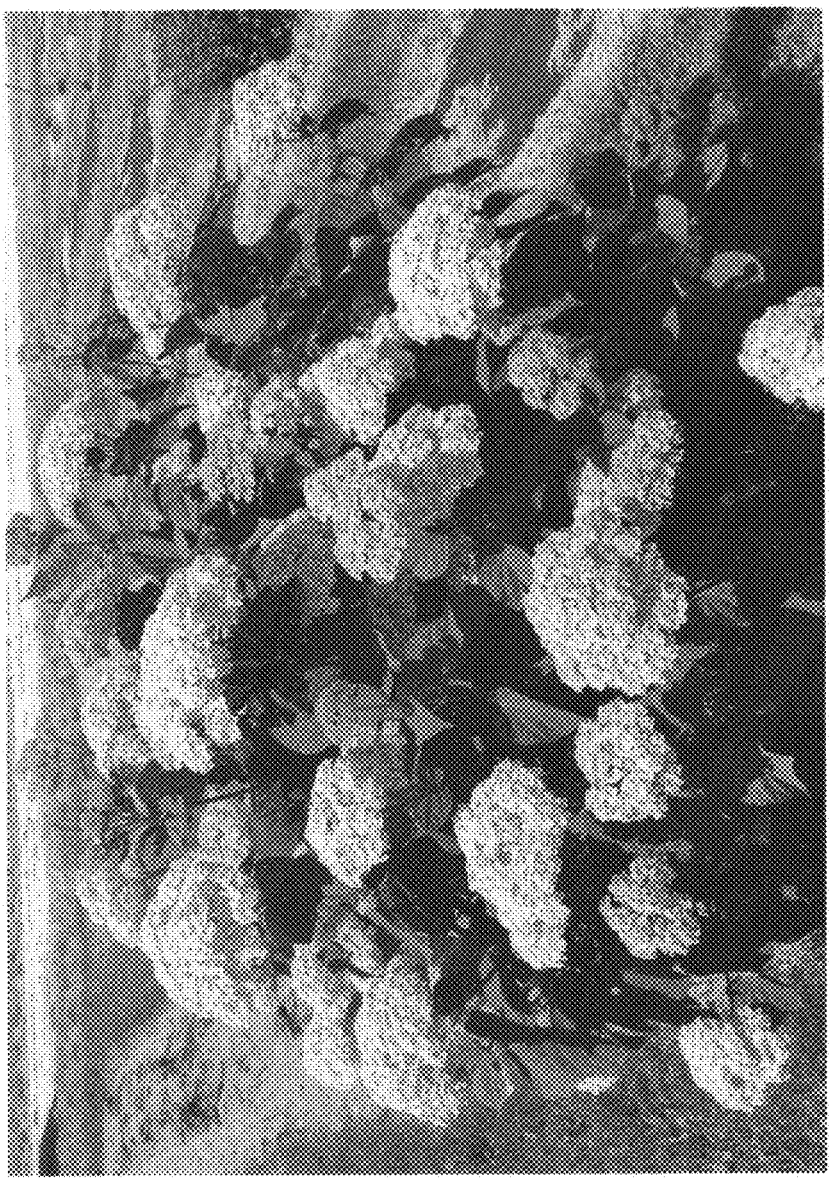
FIG. 1 shows a field grown plant of 'SMNHRL' grown outdoors in Grand Haven, Mich. at about 2.5 years of age.
Figure 2:
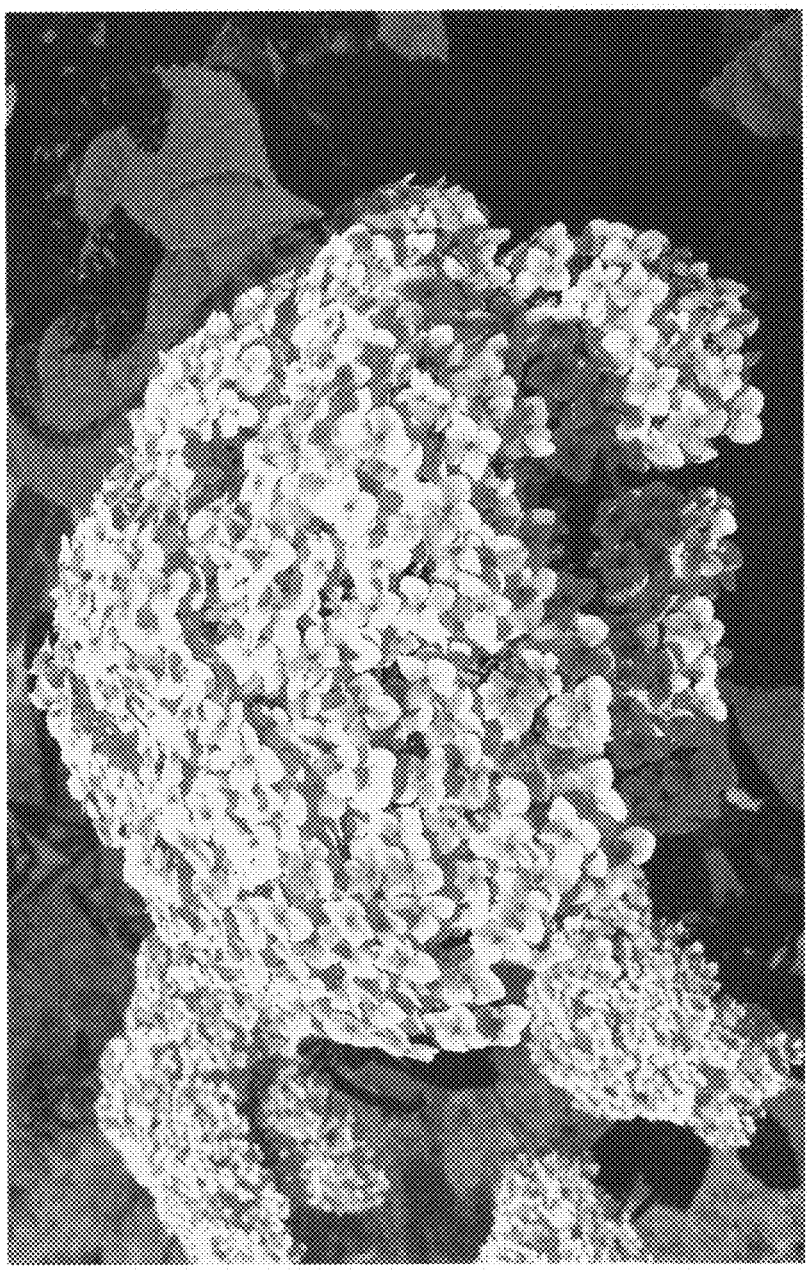
FIG. 2 shows the mature inflorescence of a field grown plant of 'SMNHRL', grown in Grand Haven, Mich.
Figure 3:
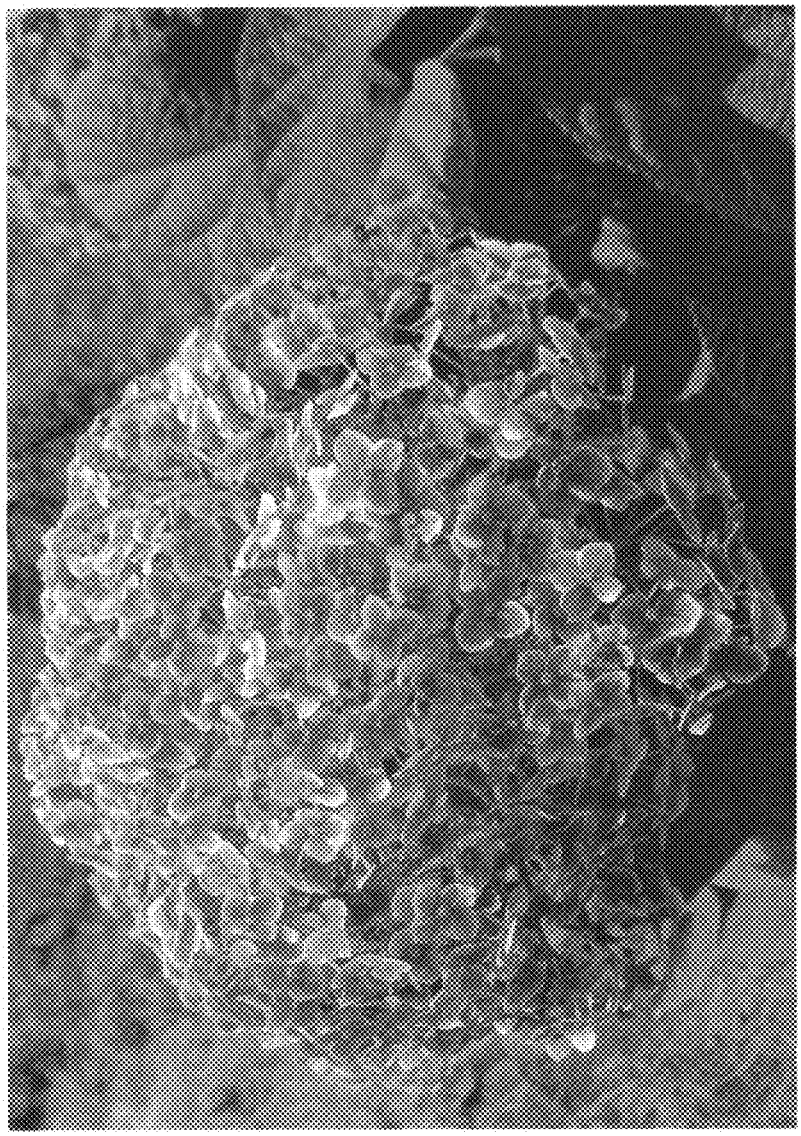
FIG. 3 shows the immature inflorescence of a field grown plant of 'SMNHRL', grown in Grand Haven, Mich.

In the following description, color references are made to The Royal Horticultural Society Colour Chart 2015, except where general terms of ordinary dictionary significance are used. The following observations and measurements describe 'SMNHRL' plants grown outdoors in Grand Haven, Mich. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Hydrangea arborescens* subsp. *radiata* 'SMNHRL'.

PROPAGATION

Typical method: Softwood cuttings.
Root initiation: Approximately 18 days.
Roots: Thick, fine, fibrous, moderately dense. White and brown in color, not accurately measured with R.H.S. chart.

PLANT

Growth habit: Upright, slightly outwards.
Height: 90 cm.
Plant spread: 105 cm.
Pot size of plant described: #3 container.
Age of plant described: Approximately 2 to 3 years.
Growth rate: Strong.
Plant vigor: Quite vigorous.
Stem:
- *Branching*.—Freely branching.
- *Shape*.—Round.
- *Color*.—Immature: RHS Yellow-Green 145A to Yellow-Green 144B. Mature: RHS Brown N200A.
- *Length*.—80 cm.
- *Width*.—5 mm.
- *Texture*.—Pubescent on new growth.
- *Internode length*.—5 to 12 cm.

FOLIAGE

Leaf:
- *Arrangement*.—Opposite.
- *Shape*.—Ovate.
- *Length*.—9 cm.
- *Width*.—7 cm.
- *Apex*.—Acuminate.
- *Base*.—Cordate/obtuse.
- *Margin*.—Denticulate.
- *Texture of top surface*.—Coriaceous.
- *Texture of bottom surface*.—Coriaceous with pronounced venation.
- *Pubescence*.—On both sides, predominantly along veins and mid-rib.
- *Color*.—Young foliage upper side: RHS Green NN137B. Young foliage under side: RHS Greyed-Green 191A. Mature foliage upper side: RHS Green NN137B. Mature foliage, upper side: RHS Greyed-Green 191A.

Venation:
- *Type*.—Pinnate.
- *Color*.—Upper side: RHS Yellow-Green 145A. Under side: RHS Yellow-Green 145B-C.

Petiole:
- *Length*.—3.5 cm.
- *Width*.—2 mm.
- *Color*.—Upper side: RHS Yellow-Green 145A, with tinges of Greyed-Orange 177A. Under side: RHS Yellow-Green 145A.
- *Texture*.—Upper side: Lightly pubescent. Under side: Lightly pubescent.

INFLORESCENCE

Natural flowering season: Summer.
Quantity of flowers: About 2500 flowers and flower buds per plant.
Inflorescence type: Mophead.
Panicle:
- *Shape*.—Umbel.
- *Height*.—7 cm.
- *Diameter*.—18 to 20 cm.

Fragrance: Sweet, perfume-like.
Sterile flowers:
- *Flowers per inflorescence*.—Around 600.
- *Aspect*.—Upright.
- *Shape*.—Round whorl.
- *Length*.—1.5 cm.
- *Diameter*.—1.5 cm.
- *Depth*.—2 mm.
- *Persistent or self-cleaning*.—Persistent.

Bud:
- *Length*.—2 mm.
- *Bud diameter*.—2 mm.
- *Bud shape*.—Round.
- *Bud color*.—RHS Greyed-Red 182B-C.

Petals:
- *Number per flower*.—4.
- *Arrangement*.—Cruciform.
- *Shape*.—Elliptic.
- *Tip*.—Acute.
- *Base*.—Cuneate.
- *Margin*.—Entire.
- *Length*.—1.25 mm.
- *Width*.—1 mm.
- *Texture*.—Upper side: Smooth. Under side: Smooth.
- *Color*.—When Opening, Upper side: RHS Red-Purple 69C. When Opening, Under side: RHS Red-Purple 69C. Fully Opened, Upper side: RHS Red-Purple 69C. Fully Opened, Under side: RHS Red-Purple 69C.

Sepal:
- *Number*.—4 to 5.
- *Arrangement*.—Cruciform/whorl.
- *Shape*.—Ovate.

*Tip*.—Acute.
*Base*.—Obtuse.
*Margin*.—Entire.
*Length*.—6 mm.
*Width*.—7 mm.
*Texture*.—Upper side: Smooth. Under side: Smooth.
*Color*.—When Opening, Upper side: RHS Yellow-Green 144B. When Opening, Under side: RHS Yellow-Green 144C. Fully Opened, Upper side: RHS Yellow-Green 144D, fading to 150C near margins. Fully Opened, Under side: RHS Yellow-Green 144D.

Pedicle:
*Length*.—1.5 cm.
*Diameter*.—1 mm.
*Angle*.—45°.
*Strength*.—Good, flexible.
*Texture*.—Smooth, slightly pubescent.
*Color*.—RHS Yellow-Green 144D.

Fertile flowers:
*Flowers per inflorescence*.—Around 1000.
*Aspect*.—Upright.
*Shape*.—Round whorl.
*Length*.—5 mm.
*Diameter*.—5 mm.
*Depth*.—2 mm.
*Persistent or self-cleaning*.—Self-cleaning.

Bud:
*Length*.—2 mm.
*Bud diameter*.—2 mm.
*Bud shape*.—Round.
*Bud color*.—RHS Greyed-Red 182B-C.

Petals:
*Number per flower*.—5.
*Arrangement*.—Whorl.
*Shape*.—Elliptic.
*Tip*.—Acute.
*Base*.—Cuneate.
*Margin*.—Entire.
*Length*.—1.25 mm.
*Width*.—1 mm.
*Texture*.—Upper side: Smooth. Under side: Smooth.
*Color*.—When Opening, Upper side: RHS Red-Purple 69C. When Opening, Under side: RHS Red-Purple 69C. Fully Opened, Upper side: RHS Red-Purple 69C. Fully Opened, Under side: RHS Red-Purple 69C.

Sepal: None.

Pedicel:
*Length*.—2 mm.
*Diameter*.—1 mm.
*Angle*.—45°.
*Strength*.—Good, flexible.
*Texture*.—Smooth, slightly pubescent.
*Color*.—RHS Yellow-Green 144D.

REPRODUCTIVE ORGANS

Sterile flower:
Stamens:
*Number*.—4 to 5.
*Filament color*.—RHS White NN155A.
*Filament length*.—2 mm.
Anthers:
*Length*.—1 mm.
*Shape*.—Rounded, dithecal, basifixed.
*Color*.—RHS Red 36B.
*Pollen*.—Moderate.
*Pollen color*.—Near RHS Red 36D.
Pistil:
*Number*.—1.
*Length*.—2 mm.
Stigma:
*Length*.—1 mm.
*Shape*.—Bi-lobed.
*Color*.—RHS White NN155A.
*Style length*.—1 mm.
*Style color*.—RHS White NN155A.

Fertile flower:
Stamen:
*Number*.—Around 10.
*Filament length*.—4 mm.
*Filament color*.—RHS White NN155A.
Anther:
*Shape*.—Rounded, dithecal, basifixed.
*Length*.—1 mm.
*Color*.—RHS Red 36B.
*Pollen amount*.—Some.
*Pollen color*.—Near RHS Red 36D.
Pistil:
*Number*.—1.
*Length*.—2 mm.
Stigma:
*Shape*.—Bi-lobed.
*Color*.—RHS White NN155A.
*Style length*.—1 mm.
*Style color*.—RHS White NN155A.
Other: Fertile flower petals shed readily.

OTHER CHARACTERISTICS

Disease resistance: Neither resistance nor susceptibility to the normal diseases and pests of *Hydrangea* has been observed.
Temperature tolerance: Typically USDA Zones 5 through 9.
Fruit/seed production: Not observed to date.

What is claimed is:

1. A new and distinct cultivar of *Hydrangea* plant named 'SMNHRL' as herein illustrated and described.

* * * * *